(12) United States Patent
Taylor

(10) Patent No.: US 7,214,243 B2
(45) Date of Patent: May 8, 2007

(54) INTERVERTEBRAL DISK PROSTHESIS

(75) Inventor: Brett Allison Taylor, Clayton, MO (US)

(73) Assignee: 3HBFM, LLC, Dayton, OH (US)

( * ) Notice: Subject to any disclaimer, the term of this patent is extended or adjusted under 35 U.S.C. 154(b) by 152 days.

(21) Appl. No.: 10/690,430

(22) Filed: Oct. 21, 2003

(65) Prior Publication Data
US 2004/0254644 A1 Dec. 16, 2004

Related U.S. Application Data

(60) Provisional application No. 60/419,556, filed on Oct. 21, 2002.

(51) Int. Cl.
A61F 2/44 (2006.01)
(52) U.S. Cl. .................................. 623/17.11
(58) Field of Classification Search ... 623/17.11–17.16
See application file for complete search history.

(56) References Cited

U.S. PATENT DOCUMENTS

| 3,867,728 A | 2/1975 | Stubstad et al. |
| 3,875,595 A | 4/1975 | Froning |
| 4,349,921 A | 9/1982 | Kuntz |
| 4,759,766 A | 7/1988 | Buettner-Janz et al. |
| 4,772,287 A | 9/1988 | Ray et al. |
| 4,911,718 A | 3/1990 | Lee et al. |
| 4,932,975 A | 6/1990 | Main et al. |
| 5,002,576 A | 3/1991 | Fuhrmann et al. |
| 5,171,281 A | 12/1992 | Parsons et al. |
| 5,258,031 A | 11/1993 | Salib et al. |
| 5,314,477 A | 5/1994 | Marnay |
| 5,370,697 A | 12/1994 | Baumgartner |
| 5,401,269 A | 3/1995 | Buttner-Janz |
| 5,425,773 A | 6/1995 | Boyd |
| 5,507,816 A | 4/1996 | Bullivant |
| 5,514,180 A | 5/1996 | Heggeness et al. |
| 5,534,029 A | 7/1996 | Shima |
| 5,534,030 A | 7/1996 | Navarro et al. |
| 5,545,229 A | 8/1996 | Parsons et al. |
| 5,554,191 A | 9/1996 | Lahille et al. |
| 5,556,431 A | 9/1996 | Buttner-Janz |
| 5,562,738 A | 10/1996 | Boyd et al. |

(Continued)

OTHER PUBLICATIONS

International Search Report issued in PCT Application No. PCT/US03/33313, dated Jan. 18, 2005.

Primary Examiner—Corrine McDermott
Assistant Examiner—Christopher Prone
(74) Attorney, Agent, or Firm—Winston & Strawn LLP

(57) ABSTRACT

A vertebral disk prosthesis with at least one member that has lateral portions coupled to each other and structured to move between contracted and expanded positions. In the contracted position, the member has a first lateral width and the end surface is narrower than the lateral width of a vertebral body of a patient. In the expanded position, the lateral portions are disposed such that the member has a second lateral width that is larger than the first lateral width and the axial end surface is configured for supporting and abutting the periphery of the body at least on both the lateral sides thereof. An expansion member is disposed between the lateral portions and configured for moving the lateral portions to the expanded position. The prosthesis is preferably also axially expandable. A method and tool for inserting the intervertebral disk prostheses are also provided.

40 Claims, 13 Drawing Sheets

U.S. PATENT DOCUMENTS

| | | |
|---|---|---|
| 5,653,763 A | 8/1997 | Errico et al. |
| 5,674,295 A * | 10/1997 | Ray et al. ............... 623/17.12 |
| 5,676,701 A | 10/1997 | Yuan et al. |
| 5,899,941 A | 5/1999 | Nishijima et al. |
| 5,980,522 A * | 11/1999 | Koros et al. .................. 606/61 |
| 5,989,291 A | 11/1999 | Ralph et al. |
| 6,039,761 A | 3/2000 | Li et al. ........................ 623/17 |
| 6,063,121 A | 5/2000 | Xavier et al. |
| 6,102,950 A | 8/2000 | Vaccaro |
| 6,113,637 A | 9/2000 | Gill et al. |
| 6,129,763 A * | 10/2000 | Chauvin et al. ......... 623/17.11 |
| 6,132,464 A | 10/2000 | Martin |
| 6,146,421 A | 11/2000 | Gordon |
| 6,156,067 A | 12/2000 | Bryan et al. |
| 6,162,252 A | 12/2000 | Kuras et al. |
| 6,296,664 B1 | 10/2001 | Middleton |
| 6,348,071 B1 | 2/2002 | Steffe et al. |
| 6,368,350 B1 | 4/2002 | Erickson et al. |
| 6,371,989 B1 | 4/2002 | Chauvin et al. ......... 623/17.11 |
| 6,375,682 B1 | 4/2002 | Fleischmann et al. |
| 6,395,031 B1 | 5/2002 | Foley et al. |
| 6,402,785 B1 | 6/2002 | Zdeblick et al. |
| 6,723,126 B1 | 4/2004 | Berry ...................... 623/17.11 |
| 6,835,206 B2 * | 12/2004 | Jackson .................. 623/17.11 |
| 2001/0016773 A1 | 8/2001 | Serhan et al. |
| 2001/0051829 A1 | 12/2001 | Middleton |
| 2002/0000944 A1 | 1/2002 | Ouchi |
| 2002/0035400 A1 | 3/2002 | Bryan et al. |
| 2002/0111683 A1 | 8/2002 | Ralph et al. |
| 2002/0111684 A1 | 8/2002 | Ralph et al. |
| 2002/0111685 A1 | 8/2002 | Ralph et al. |
| 2002/0111687 A1 | 8/2002 | Ralph et al. |

* cited by examiner

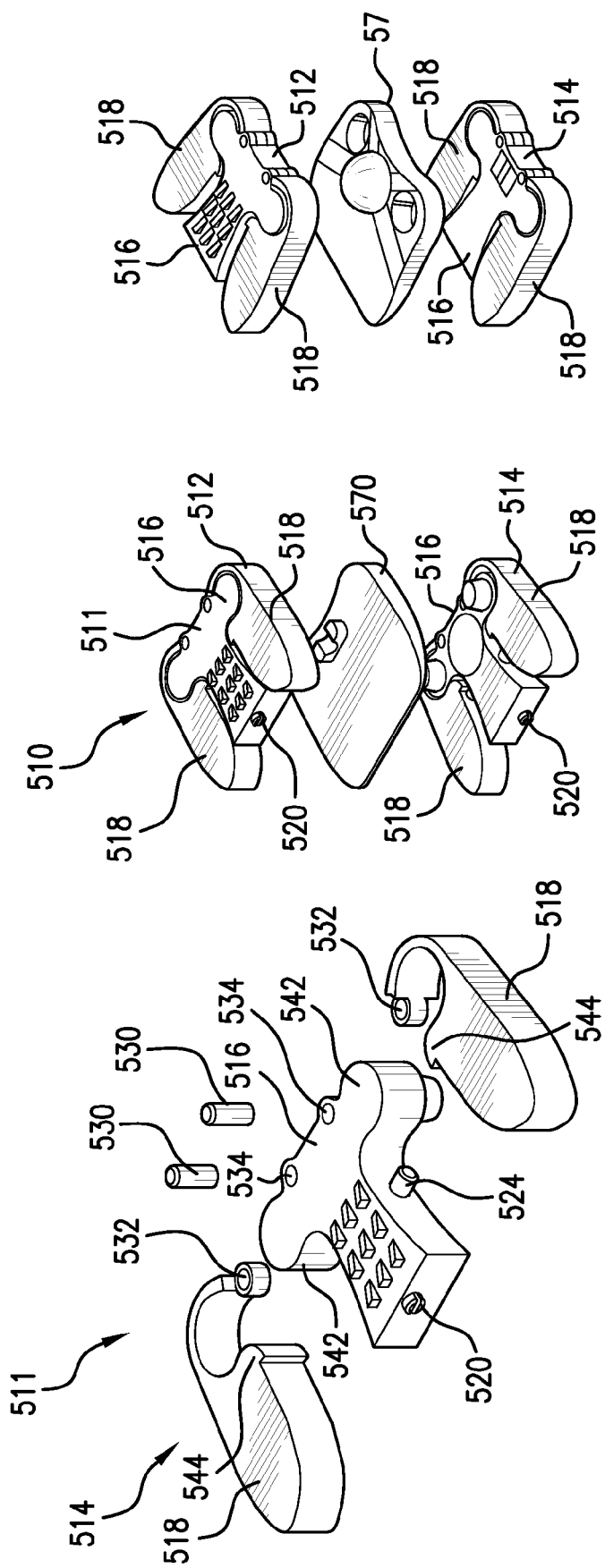

INTERVERTEBRAL DISK PROSTHESIS

CROSS-REFERENCE TO RELATED APPLICATION

This application claims priority under 35 U.S.C. §119(e) to provisional application Ser. No. 60/419,556, filed Oct. 21, 2002, which is incorporated herein by reference.

FIELD OF THE INVENTION

The present invention relates to a prosthesis for association with the bone structure of a patient, and more particularly to an intervertebral disk prosthesis that is expandable to an implantation configuration.

BACKGROUND OF THE INVENTION

Procedures exist for replacing diseased intervertebral disks in which the disk material is typically removed from between adjacent vertebral bodies, and the adjacent bodies are fused. This has been done with a cage placed in between the bodies to fix them to each other, generally to support and promote fusion between the adjacent vertebrae.

U.S. Pat. No. 6,102,950, for example, discloses an intervertebral fusion device. A wedge body is nested within a cage component. A contraction mechanism with a threaded shaft draws the wedge body into the cage component to increase the angle between upper and lower members of the cage component to achieve a proper angle of lordosis. The cage component also has a plurality of spines, each with a spike facing outwardly through passages. Ramps on the wedge deploy the spikes into the endplates of the vertebral bodies. U.S. Pat. Nos. 5,653,763 and 5,554,191 disclose cages that employ different means to expand the cages vertically.

While fusion cages provide no mobility between the fused vertebrae, other prostheses have been developed to permit motion between the adjacent vertebrae. One of these is known as the Link, sold by the Link Spine Group, Inc., has top and bottom plates that are implanted between vertebral bodies, and between which a core is placed. The plates and the core contact at rounded surfaces to allow the plates to move about the core.

These devices have a fixed width. Due to the positioning of tendons and vascular anatomy, the opening available on the anterior side of the spinal column for implanting the prosthesis is narrower than the width of the bodies, and the prosthesis are narrower as well. U.S. Pat. No. 6,395,031 shows an intervertebral spacer that is expandable laterally once implanted. The spacer has a fixed height, and several are inserted to contact the face of the vertebral bodies.

Patent Application Publication No. US 2002/009944 A1 shows a modular interbody implant with a fixed height and made from bone, and having lateral spacers that receive therebetween a connecting member. The three pieces taught as being assembled between the vertebrae.

Accordingly, there is a need for an improved disk prosthesis that can facilitate implantation by providing both axial and lateral expansion, and that provides improved support to the vertebral bodies by maximizing the surface area contact between the prosthesis and adjacent vertebrae, and by supporting the vertebrae at the portion where the bone is strongest.

SUMMARY OF THE INVENTION

The present invention relates to an intervertebral vertebral disk prosthesis that facilitates implantation within a patient that may be a human or an animal and with improved longevity. The preferred embodiment has a body contacting member with an axial end surface configured for engaging a vertebral body. The contacting member comprises first and second lateral portions connected to each other movably between a contracted and an expanded position. An expansion member is disposed between the lateral portions and configured for moving the lateral portions to the expanded position. Additionally, it is preferred that the lateral members be pivotally or flexibly connected to each other possibly with a central body therebetween for pivoting from the contracted to the expanded position. In a preferred contacting member, first and second living hinges preferably connect the first and second lateral portions, respectively. The contacting member of the preferred embodiment also has a central portion connected by the living hinges between the lateral portions.

In the contracted position, the contacting member has a first lateral width and the end surface is narrower than the lateral width of a vertebral body of a patient. In the expanded position, the lateral portions are disposed such that the contacting member has a second lateral width that is larger than the first lateral width, and the axial end surface is configured for supporting and abutting the periphery of the body, preferably at least on both the lateral sides thereof.

The preferred shape of the contacting member in the expanded position generally corresponds to the periphery of the vertebral body. In the expanded position, the lateral portions are configured for abutting and supporting at least about 50% of the periphery of the body.

The preferred expansion member comprises a wedge receivable between the lateral portions for moving the lateral portions to the expanded position. A threaded fastener is connected between the wedge and the contacting member such that rotation of the fastener moves the wedge with respect to the first lateral portion for moving the lateral portions to the expanded position. This wedge has a laterally elongated cross-section extending along a plane normal to a direction of movement of the wedge, and also preferably an axial surface that is inclined with respect to the axis for moving a gripping portion of the contacting member against the vertebral body.

The wedge and contacting member can be associated for preventing withdrawal movement of the wedge with respect to the contacting member to resist or the lateral portions from moving towards the contracted position. To achieve this, the wedge and contacting member may comprise a ratchet configured for allowing movement of the wedge with respect to the lateral portions in a first direction for moving the lateral portions to the expanded position, and for restricting or movement of the wedge in the opposite direction.

Preferably, the lateral portions include a first wedge support portion and the wedge comprises a second wedge support portion. In the preferred embodiment, one of the wedge support portions includes a key, and the other comprising a keyway configured and dimensioned for slideably receiving the key to provide axial support to the wedge.

One embodiment of the invention is a cage configured for locking adjacent vertebral bodies together, with the axial end surface comprising first and second axial end surfaces facing in opposite directions for abutting and supporting the adjacent vertebral bodies. Another embodiment includes another member disposed with respect to the contacting member for abutting and supporting adjacent vertebral bodies, with the contacting member and another member are pivotally connected for allowing the adjacent vertebral bodies to pivot with respect to each other.

In this pivotable embodiment, the axial end surfaces of two contacting members face in opposite directions for abutting and supporting adjacent vertebral bodies. A pivot limiter is preferably disposed between the contacting members and comprises a sloped surface facing a first of the contacting members. The first contacting member and the pivot limiter are pivotally connected, and the sloped surface is configured and associated with the contacting members for allowing and limiting pivoting between the first contacting member and the pivot limiter. The preferred first contacting member comprises a central portion disposed between the lateral portions, and the central portion is connected to the other member.

A pivot pivotally connects the contacting members for axial rotation in this embodiment. Also, at least one protrusion is associated with one of the contacting members and is received in an opening, preferably, of the other of the contacting members. The opening is larger than the protrusion in a rotational direction about the pivot for permitting and limiting the axial rotation. The preferred pivot comprises a universal pivot.

The preferred embodiment can be expanded along two axes, and preferably includes an axial portion configured for moving between a retracted and an extended position that are spaced axially from each other. In the retracted position, the prosthesis has a first axial height. In the extended position, the prosthesis has a second axial height that is greater than the first axial height.

The preferred axial portion comprises a gripping portion disposed and configured for engaging and gripping an interior portion of the vertebral body face in the expanded position. The wedge in this embodiment has lateral and axial wedge surfaces cammingly associated with the lateral and axial portions for camming the lateral and gripping portions to the expanded and extended positions.

Preferably, a bushing is disposed between and in supportive association with the contacting members when the prosthesis is implanted between the bodies. The bushing comprises a gel and is configured for absorbing shock between the adjacent vertebral bodies. In the preferred embodiment, the bushing is slideable with respect to the first contacting member for reducing shearing within the bushing.

An inventive instrument for implanting a prosthesis has first and second fastener drivers configured for engaging and driving first and second fasteners for adjusting a dimension of the prosthesis. The instrument also has a spacer connected between the first and second drivers and configured and dimensioned for positioning between the contacting members of the prosthesis. The spacer is configured for maintaining the relative position of the contacting members preferably during implantation and adjustment of the gripping member.

In a preferred method, the prosthesis is positioned between adjacent vertebral bodies and is expanded both axially and laterally to engage the vertebrae. The spacer of the instrument is preferably placed between the contacting members to keep them in the relative position with respect to each other. The wedge is moved with respect to at least one of the contacting members for expanding at least one dimension of the prosthesis when the prosthesis is disposed between the bodies with the spacer placed between the contacting members. The instrument and spacer are removed from the prosthesis as the surgery is completed.

The present invention thus provides improved support to the spinal column, while providing a smaller size to aid implantation, and an expanded size to obtain the optimum shape after implantation.

BRIEF DESCRIPTION OF THE DRAWINGS

FIG. 17 is an exploded view of an alternate embodiment;

FIG. 18 is a top exploded view of an alternate embodiment; and

FIG. 19 is a bottom exploded view of the alternate embodiment of FIG. 18.

DETAILED DESCRIPTION OF THE PREFERRED EMBODIMENTS

Figure 1:
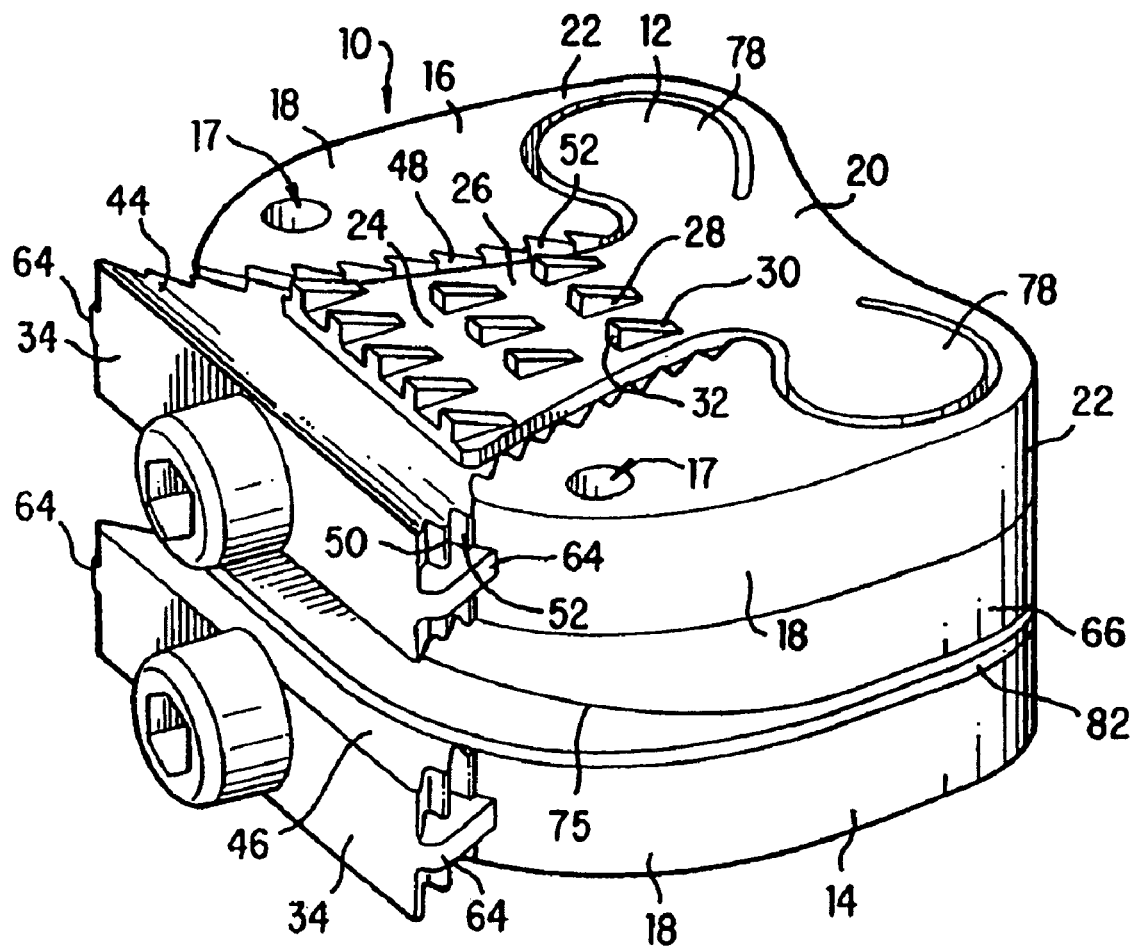
FIG. 1 is a top anterior perspective view of a preferred embodiment of a prosthesis constructed according to the invention.

Referring to FIG. 1, the preferred embodiment of the invention is a vertebral disk prosthesis 10, which includes at least one member and, preferably, a top and bottom members. The members preferably include top and bottom endplates 12,14, respectively, which are preferably made from titanium or another durable and hard material.

Each endplate 12,14 has an axial end surface 16 configured for engaging a vertebral body when implanted along a spinal column. Also, openings 17 are preferably provided to foment bone growth therethrough to fuse to the endplates 12,14.

The endplates 12,14 include portions that are movable to extend and contract the horizontal dimensions of the implant. Preferably, the endplates 12,14 include left and right lateral portions 18 that may be movably connected to each other, or are more preferably moveably connected to a central portion 20. The lateral portions 18 can be connected by hinges, such as living hinges 22, which are preferably resiliently spring biased to position the lateral portions 18 in a contracted position.

The living hinges 22 shown extend horizontally around the outside of the central portion 20 and are connected to the posterior side thereof to increase the flexible portion of the hinges 22 and to increase the fraction of the endplates 12,14 disposed at the lateral sides thereof that expands laterally when the lateral portions 18 are moved outwardly. Preferably, most or substantially all of this fraction of the endplates 12,14 disposed on the lateral edges thereof, including the portion of the hinges 22 disposed at the lateral edges, expands outwardly when the lateral portions 18 are also moved outwardly. In alternative embodiments, other hinge arrangements can be employed, preferably with a spring element to move the lateral portions 18 toward each other to contract the prosthesis.

A gripping portion 24 preferably extends from the central portion 20 and includes an axially facing surface 26. The axially facing surface 26 preferably has a texture or a shape to promote engagement with the face of a vertebral body. In the embodiment shown, scales 28 extend axially from the gripping portion 24 for engaging and gripping the interior portion of the face of the vertebral body. The scales 28 have a shallow ramp 30 on a posterior side thereof, to permit the introduction of the prosthesis 10 into the intervertebral space, and a steeper surface 32, such as a vertical side or a side angled to face away from the vertebral body towards the axially facing surface 26, to impede or prevent withdrawal of the prosthesis 10 from engagement with the vertebral body. The scales 28, and preferably the lateral sides of the scales 28, are preferably configured to resist lateral movement of the prosthesis 10 with respect to the adjacent vertebral body once implanted. In alternative embodiments, the axial surface 26 can have other protrusions or indentations configured for engaging the body face.

The gripping portion 24 is preferably cantilevered from the central portion 20 and is pivotably axially, preferably pivoting about a laterally extending axis, to engage the body face when implanted. The gripping portion 24 is resiliently hinged from the central portion 20 to naturally retain a retracted position to minimize the axial height of the prosthesis 10, but can be biased to pivot to an extended position in which the prosthesis 10 has a greater axial height.

Figure 4:
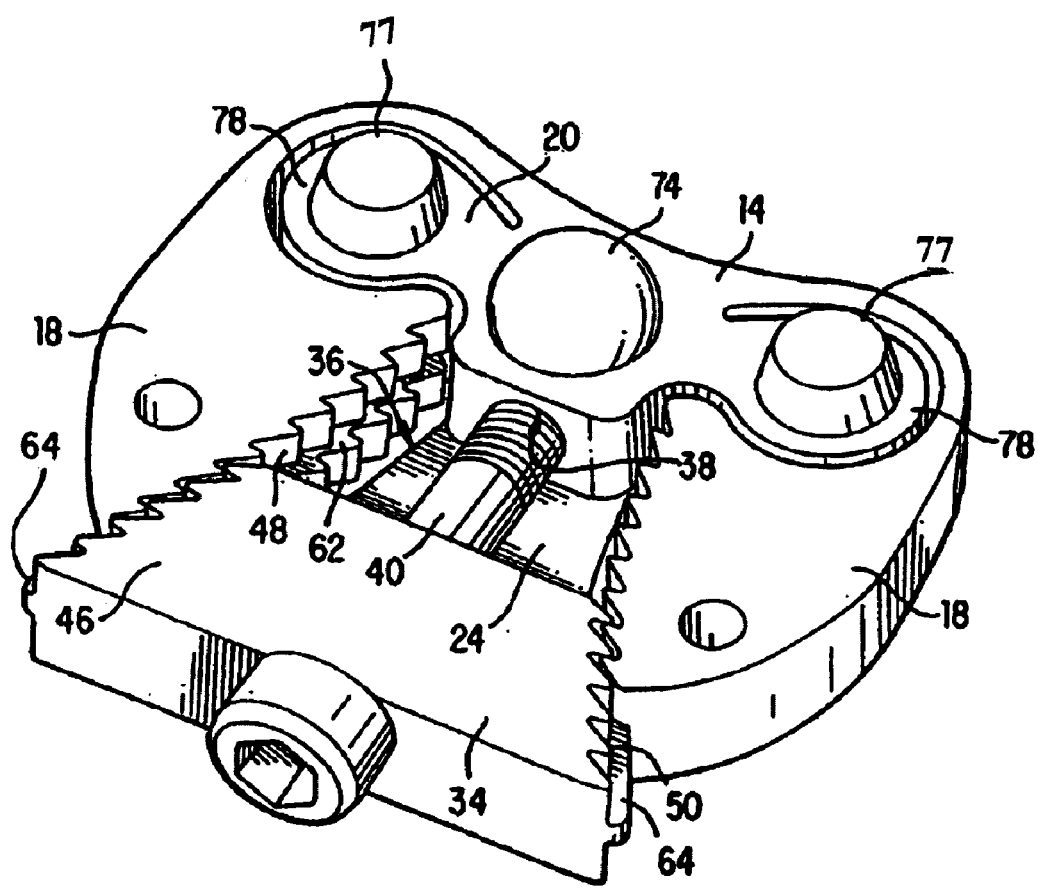
FIG. 4 is a top view of one of the endplates thereof.

In the preferred embodiment, an expansion member, such as a wedge 34, is received between the lateral and gripping portions 18, 24 in a wedge space 36, as shown in FIG. 4. The wedge 34 is preferably made from titanium or another durable and hard material. Although independent wedges or other expansion members may alternatively be employed for the various movable parts in the contacting members, a single wedge 34 is preferably used to contact and move all of the lateral and gripping portions 18, 24 of each endplate 12,14 by a single adjustment of the wedge 34.

Figure 2:
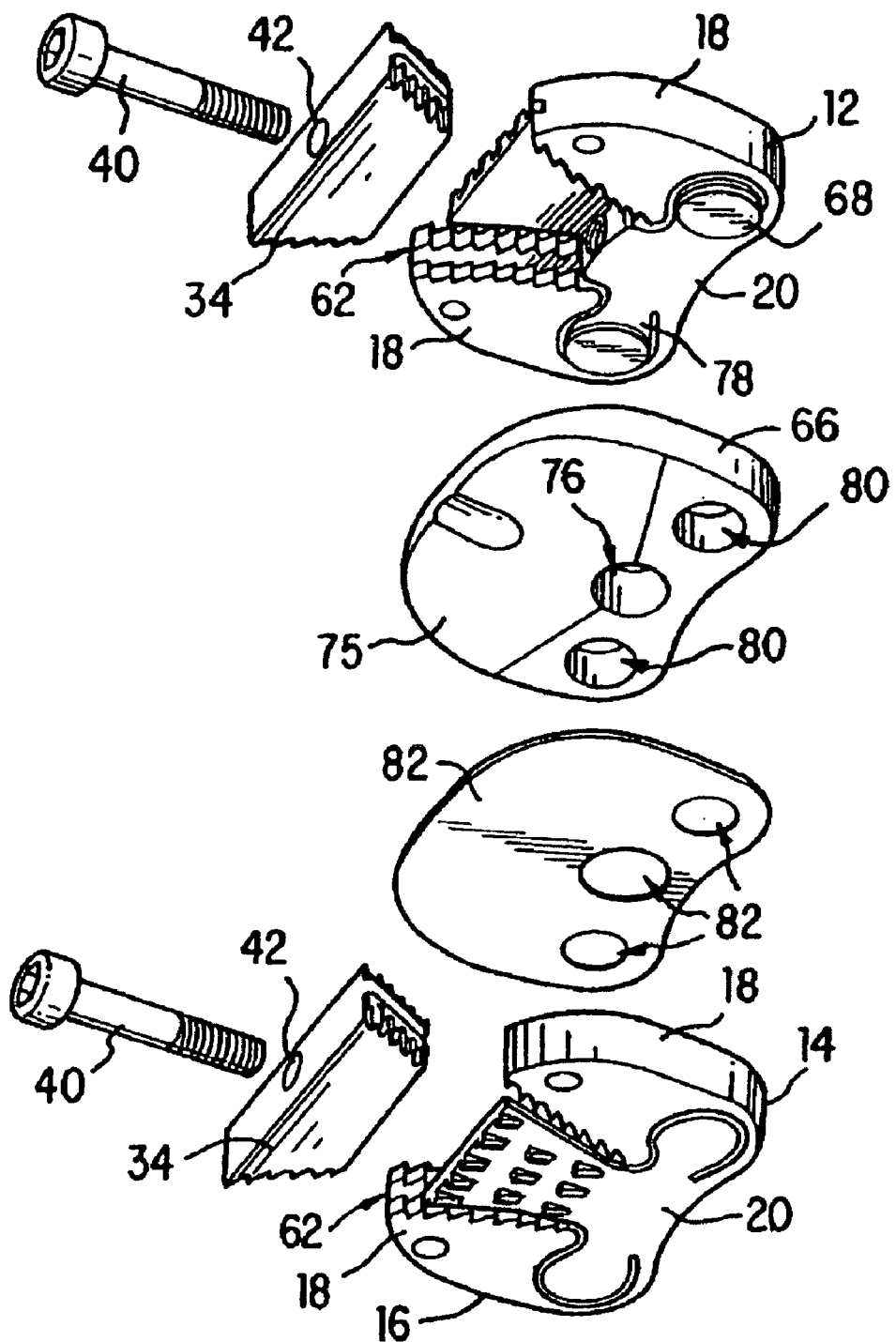
FIGS. 2 and 3 are respectively bottom and top perspective exploded views thereof.
Figure 3:
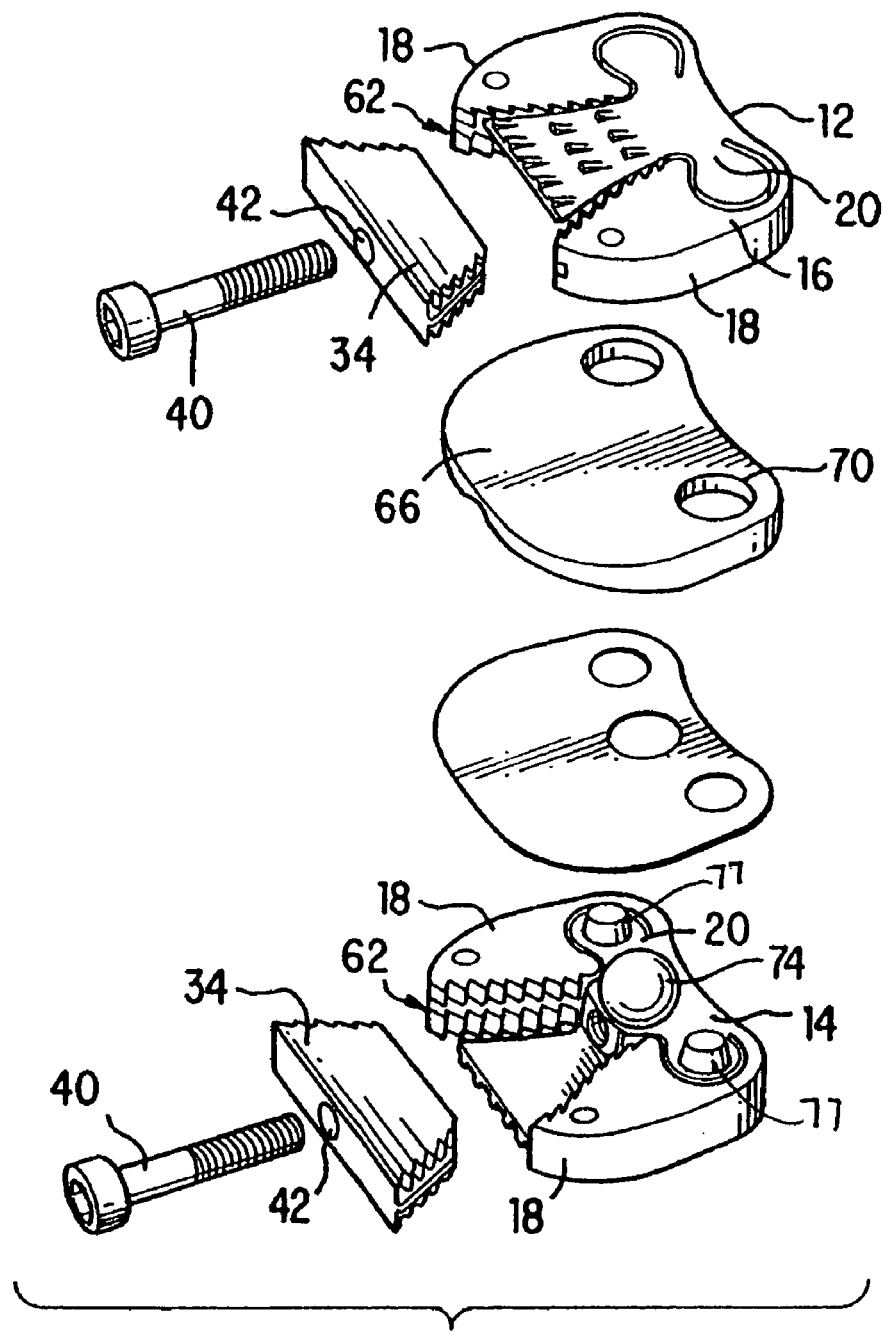

The wedge space 36 is generally tapered laterally. Additionally, the preferred central portion 20 defines a threaded bore 38 to receive a threaded fastener 40 that is received through a bore 42 in the wedge 34, which is shown in FIGS. 2 and 3. The fastener 40 is configured such that rotation thereof moves the wedge 34 with respect to the endplates 12,14, and preferably with respect to the lateral and gripping portions 18,24. Other mechanisms can alternatively be used to move the wedge 34 with respect to the respective endplate 12,14, and these mechanisms are preferably disposed laterally and axially within the outer dimensions of the other parts that form the prosthesis so that the mechanisms themselves do not increase the width or the height of the prosthesis.

Figure 5:
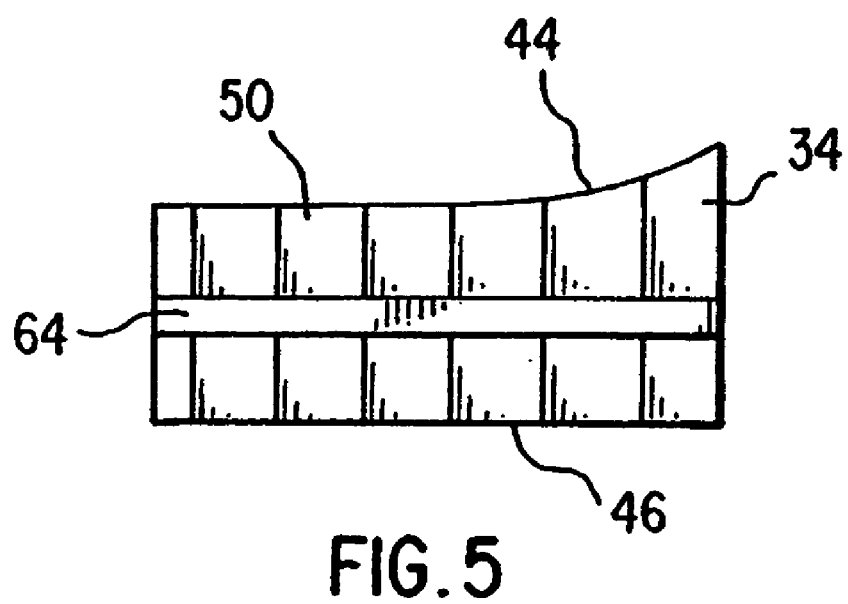
FIG. 5 is a left side view of a wedge of the prosthesis.

The wedge 34 preferably has an elongated and preferably rectangular cross-section along a plane that is normal to the movement path of the wedge 34 into the endplate 14. Preferably, the elongated dimension extends laterally, and the cross-section basically has four sides. The wedge 34 is also tapered towards a posterior direction both laterally and along an outwardly axially facing surface 44 that contacts the gripping portion 24. As shown in FIG. 5, surface 44 is concave, with the taper becoming steeper towards the anterior side. Thus, the wedge 34 cams the gripping portion 24 at an increasing rate as the wedge 34 is driven into the endplate 12,14. Additionally, the posterior end of the surface 44 is preferably substantially aligned with the direction of movement of the wedge 34 into the endplate 12,14 so as to not cam the gripping portion 24 significantly during the early travel of the wedge 34. An axially facing surface 46 of the wedge 34 that faces the interior of the prosthesis 10 may be flat and preferably does not protrude from the endplate 12,14.

The lateral portions 18 have contact faces 48 that are preferably disposed at an angle to the axis of the fastener 40 and the direction of motion of the wedge 34 into the endplate 12,14. Faces 48 preferably follow a convex curve, preferably being disposed and configured to contact the tapered lateral sides 50 of the wedge 34 at a generally constant angle of contact as the wedge 34 is moved within the endplate 12,14. Thus, the taper of the wedge space 36 in the embodiment shown is greater at the anterior side than at the posterior side.

In addition, the preferred wedge 34 and faces 48 of the lateral portions 18 are associated for preventing withdrawal movement of the wedge 34 with respect to the endplate 12,14. This can be achieved by ratchet portions 52 of the lateral portions 18 and wedge 34 that engage each other to allow progressive introduction of the wedge 34 into the wedge space 36, but resist extraction therefrom. Teeth of the ratchet portions 52 are configured to slide against each other when the wedge 34 is moved posteriorly, but to catch each other when the wedge 34 is moved anteriorly. Alternative shapes and structures associated with each other between the lateral portions 18 and the wedge 34 may be employed to releasably engage each other, such as bumps or a ratchet that allows movement in two directions to provide one or more stable positions of the wedge 34. A ratchet may be employed between the wedge 34 and the gripping portion 24 or between the wedge 34 and another portion of the prosthesis 10.

Figure 6:
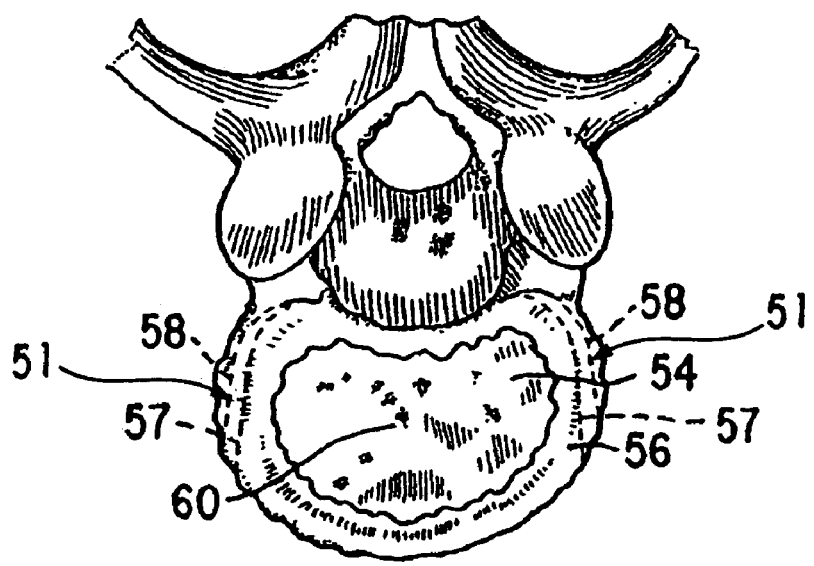
FIG. 6 is an end view of a vertebra, showing the implantation position of the prosthesis.

As shown, generally in FIG. 6, when the wedge 34 is moved into the endplate 12, 14, the wedge 34 cams the lateral portions 18 outwardly from a contracted position 57 to an expanded position 58. In the contracted position 57, the axial end surface 16 and the lateral widths of the prosthesis 10 and the endplate 12, 14 are narrower than the lateral width of a vertebral body 54. In the expanded position 58, the lateral portions 18 are disposed such that the axial end surface 16 and the lateral widths of the prosthesis 10 and the endplate 12, 14 have lateral widths that are larger in the contracted position 57, and the axial end surface 16 is configured for supporting and abutting the periphery 56 of the body 54, preferably at least at the lateral sides 51 thereof. The endplates 12, 14 and its axial end surface 16 preferably also support the body periphery 56 at the posterior and anterior sides as well, or along a portion thereof In the expanded position 58, the axial end surface 16 has an outer edge portion that generally corresponds to the periphery 56 of the vertebral body 54. Preferably, in the expanded position 58 the lateral portions 18 are configured for abutting and supporting at least about 50% of the periphery 56 of the body 54, more preferably at least about 60%, and most preferably at least about 75%, and preferably less than about 95%. One embodiment is configured for abutting and supporting between about 75% and 90%, and preferably does not substantially extend laterally or posteriorly beyond the body endplate periphery 56.

The implanted width and height of the prostheses 10, with the lateral and gripping portions 18, 24 expanded and extended, is selected according to the anatomy of the patient. Preferably, the lateral width of the prosthesis 10 is between about 20 mm and 50 mm for a lumbar disk prosthesis, and between about 10 mm and 30 mm for a cervical disk prosthesis. The preferred axial height of the prosthesis 10 is at least about 10 mm. As shown in FIG. 6, the posterior side of the prosthesis 10 is concave to follow the peripheral shape of the vertebral body 54 and leave space for the spinal foramen and spinal chord.

The posterior movement of the wedge 34 also cams the gripping portion 24 axially outwardly from the prosthesis 10 from a retracted position to an extended position. The gripping portion 24 thus pivots to engage and grip preferably an interior portion 60 of the face of the vertebral body 54. With the gripping portion 24 in the extended position, the prosthesis 10 has an axial height that is greater than with the gripping portion 24 in the retracted position. Preferably, the axial height of the prosthesis 10, not including the gripping portions 24 and preferably measured at the periphery 56 of the axial end surfaces 16 is about between 9 mm and 18 mm for a lumbar disk prosthesis, and about between 5 mm and 10 mm for a cervical disk prosthesis.

The expanded and extended lateral width and axial height of the prosthesis in the implanted configuration, including the lateral and gripping portions 18, 24, is preferably at least about 5% and more preferably at least about 10% greater than in the implantation configuration, with the lateral and gripping portions 18, 24 contracted and retracted. The lateral width and axial height is preferably at most about 40% greater, and more preferably at most about 25% greater in the implanted configuration than in the implantation configuration, also including the lateral and gripping portions 18, 24. The anterior/posterior depth of the prosthesis 10, excluding the wedge 34, is preferably not changed by more than about 10%, and more preferably about 5%.

The wedge 34 is supported axially by a portion of the prosthesis 10. Preferably, the lateral portions 18 include keyways 62 configured to slideably receive elongated keys 64 that protrude from the lateral sides 50 of the wedge 34. The keys 64 and keyways 62 provide axial support to the wedge 34. In alternative embodiments, another portion of the prosthesis 10, such as part of the central portion 20 or another member disposed adjacent the endplate 12, 14 may provide support. The keys 64 protrude laterally from the wedge 34 near the middle or the lateral sides 50 measured axially, but can protrude from other portions thereof. Also, an alternative embodiment can have a key or other protrusion extending from the lateral portion 18 and received in the wedge 34.

The two endplates 12, 14 are preferably pivotably associated with each other to allow the adjacent vertebrae between which the prosthesis 10 is implanted to be able to rotate and bend to achieve the motion similar to that available with a healthy disk. One contacting member includes a spacer 66 that has a circumferential edge that generally follows the shape of the endplate 12 with the lateral portions 18 in the contracted position 57, and which is preferably no wider laterally than the endplate 12 in the contracted position 57. The spacer 66 is preferably made from a plastic or a ceramic, such as, but not limited to, a polyethylene, a polyethylketone ("PEK"), pyrolytic carbon, alumina, zirconia and pyrolytic carbon ceramics, or other low friction material for permitting articulation with endplate 14.

The spacer 66 is preferably fixed to the central portion 20 of endplate 12, such as by attachment to protrusions 68 extending from lateral extensions 78 of the central portion 20, shown in FIG. 2, and openings 70, shown in FIG. 3. The protrusions 68 and openings 70 can be press fit or adhered to each other, or another type of connection can be used to substantially fix the endplate 12 and the spacer 66 when the prosthesis 10 is implanted.

The spacer 66 is pivotally connected to the other endplate 14. Preferably, the spacer 66 and endplate 14 are connected for allowing the adjacent vertebral bodies 54 to pivot with respect to each other. The preferred pivot is a universal pivot and allows flexion, extension, lateral bend, and axial rotation of the endplates 12, 14 and of the vertebrae to which they are attached. The embodiment shown of the universal pivot has a spherical segment ball and socket connection. The connection may, however, have a similar shape such as an ellipsoid. Referring to FIGS. 2–4, the central portion 20 of endplate 14 has a ball member 74, comprising a segment of a sphere, which is received in a preferably spherical socket 76 of the spacer 66. The socket 76 preferably extends passed the major diameter of the ball member 74 to retain the ball member 74 in a snap-fit connection to prevent separation thereof and dislocation when implanted.

The facing surfaces of the spacer 66 and endplate 14 preferably have several tapered spaces therebetween to permit limited bending therebetween. Preferably, the side of the spacer 66 facing the endplate 14 includes a surface 75 that slopes away from the endplate 14 in a direction away from the pivot. Surfaces 75 of the spacer 66 are also disposed with respect to the endplate 14 to permit limited bending. The preferred surfaces 75 are curved away from the endplate 14 towards a lateral direction. Preferably, the spacer 66, acting as a pivot limiter, and the endplate 14 are associated to permit up to about between 5° and 15° of forward flexion and more preferably up to about between 10° and 13° of flexion; and up to about between 2° and 5° of rearward extension and also a lateral bend in each direction, and more preferably up to about 3°. Preferably, a minimum, at least about 1° of flexion, extension, and bend is allowed, and more preferably at least about 2° is allowed.

Limited axial rotation is also permitted between endplates 12, 14. Lugs 77 configured and positioned to contact a limiter wall disposed between endplate 14 and the spacer 66 permit the limited axial rotation between the endplates 12, 14. Preferably the lugs 77 extend generally axially from lateral extensions 78 of the central portion 20 of the endplate 14 and are tapered towards their tips. Limiter openings 80 of the spacer 66, shown in FIG. 2, comprise the limiter walls and are sufficiently larger that the lugs 77 to limit the axial rotation preferably to between about 0.50 to each side and 2° to each side, and more preferably to about 1°. The taper on the lugs 77 limit the axial rotation more when there is lateral bend between the endplates 12, 14. Other pivot limiting systems can alternatively be used to limit the rotation or pivoting in any of the desired directions.

A bushing 82 is preferably disposed between the spacer 66 and endplate 14 in a supporting association therebetween at least when the endplate 14 and spacer 66 are pivoted and resting against each other. The bushing 80 preferably comprises a gel, which may be contained in an envelope if the gel is flowable, and is configured for absorbing shock between the adjacent vertebral bodies 54 and between the endplate 14 and spacer 66. In the preferred embodiment, the bushing 82 is slideable with respect to the endplate 14 and is not adhered or otherwise positively fixed thereto. This can reduce shearing within the bushing 82 and extend its life. The bushing 82 shown in FIG. 2 is retained in position by openings 83, which receive the ball member 74 and lugs 77.

To implant the prosthesis 10 through an endoscopic or laparoscopic procedure, a surgeon preferably performs a disk resection or incises the anulus of the disk to create a window the size of the prosthesis 10 collapsed in the implantation configuration. The nuclear gelatinous core of the disk is removed, and the faces of the endplates 12, 14 of the vertebral bodies 54 are cleared of cartilage, exposing the cortical bone of the vertebral endplate 12, 14. The cortex is breached in the center of the vertebral endplate 12, 14, exposing cancellous bone.

The surgeon then inserts the prosthesis 10 through an incision preferably in the anterior side of a patient's body with the lateral portions 18 contracted and the gripping portions 24 retracted in the implantation configuration. The incision need only be large enough to fit the contracted prosthesis 10. This facilitates the insertion of the prosthesis 10 in the space between the adjacent vertebral bodies 54 from which the disk has been removed, allowing the prosthesis 10 to pass easily around vasculature and ligaments between the vertebrae. Once the prosthesis 10 is positioned between the vertebrae, the fasteners 40 are rotated to displace the wedges 34 into the respective prosthesis endplates 12, 14, expanding the lateral portions 18 and extending the gripping portions 24 to the implanted configuration.

The preferred lateral width of the prosthesis 10 is obtained when the endplates 12, 14 are wide enough to contact and support the lateral sides 51 of the vertebral body 54, where the bone is stiffer, which improves the longevity of the implantation as the bone is better able to support weight along its outer edges. When this width is obtained, the gripping portions 24 preferably also have extended into the softer bone at the interior of the vertebral body faces, gripping them to inhibit or prevent displacement of the implanted prosthesis 10.

Figure 7:
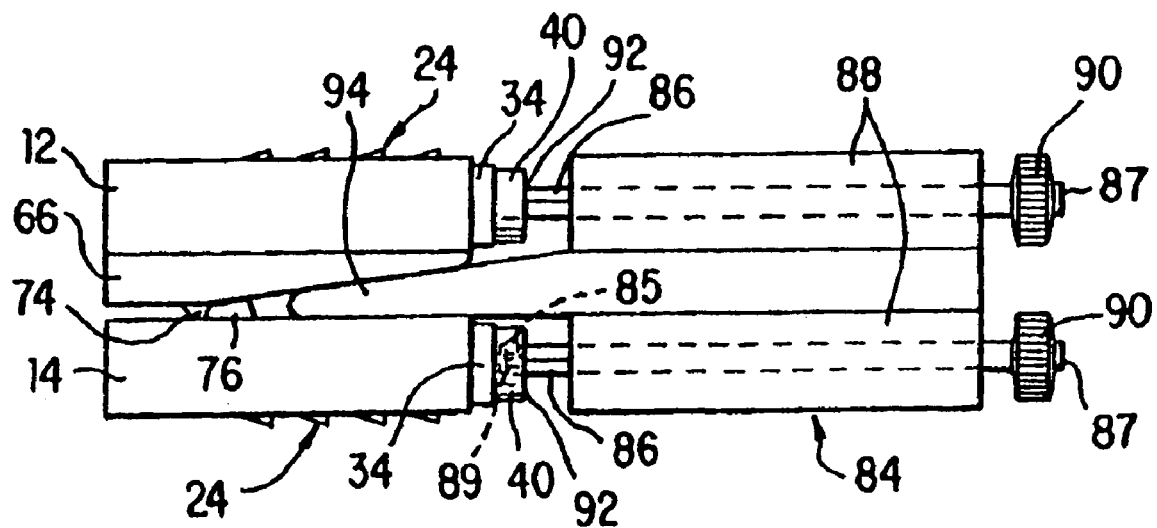
FIG. 7 is a left side view of the prosthesis with instrumentation for its implantation.

Referring to FIG. 7, a preferred instrument 84 to implant the prosthesis 10 comprises fastener drivers 86, such as hexagonal bolt drivers, where fasteners 40 are bolts with hexagonal driver openings in the bolt heads. Preferably, the drivers 86 are substantially parallel, and are aligned to simultaneously engage both fasteners 40. The drivers 86 extend through driver housings 88, and have manipulable handle portions 90 at the opposite side from fastener engagement ends 92. The handle portions 90 can be configured to be rotated by another tool in an alternative embodiment.

A positioning wedge 94 extends distally from between the drivers 86 and is configured to keep the fit between the spacer 66 and the endplate 14 to keep the endplates in substantial axial alignment and to support the endplates 12,14 as the gripping portions 24 are extended axially to engage the bone. The configuration of the positioning wedge 94, which may be tapered or untapered, and the positioning of the drivers 86 allows the fasteners 40 to be rotated while the endplates 12,14 are substantially parallel, or at an angle desired for implantation.

Preferably all contact between the implantation instrument 84 and the prosthesis 10 is at the interior of the prosthesis 10, as well as potentially at the anterior side thereof preferably at a location displaced from the lateral edges. Thus, the implantation instrument 84 does not take up any lateral, posterior, or axial end space during implantation. After the wedges 34 are positioned as desired, the implantation instrument 84 is withdrawn.

The implantation instrument 84 also preferably includes a releasable locking mechanism to lock and release from the fasteners 40 or other portion of the prosthesis 10. A preferred embodiment has locking balls 85 that are held in a position displaced laterally from the heads of the drivers 86 to catch in grooves in the heads of the fasteners 40. A manually operable release button 87 is provided to mechanically release the balls 85 from the extended locked position, preferably by sliding a cam 89 adjacent the balls 85 to allow the instrument 84 to be disengaged from the prosthesis 10.

Figure 8:
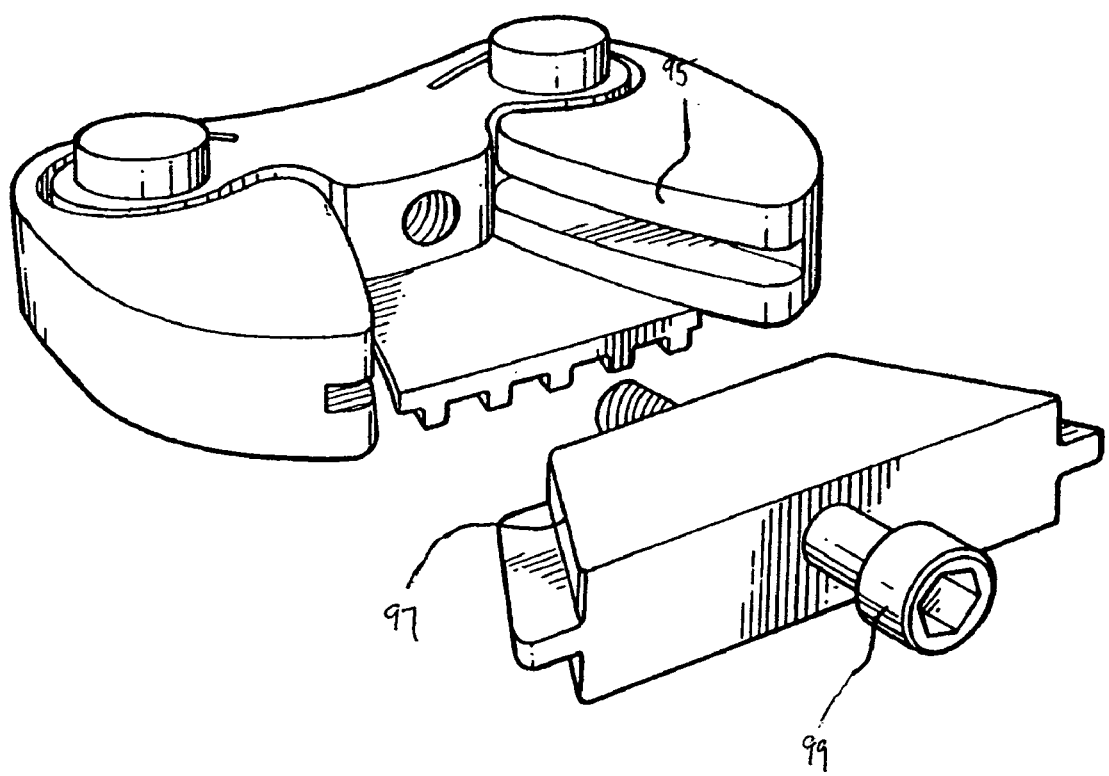
FIG. 8 is a perspective view of an endplate of another embodiment of the invention.

FIG. 8 shows another embodiment of the invention with smooth curved surfaces of the lateral portions 95 to contact smooth tapered surfaces of the wedge 97. In this embodiment, the position of the wedge 97 is exclusively controlled by the fastener 99.

Figure 9:
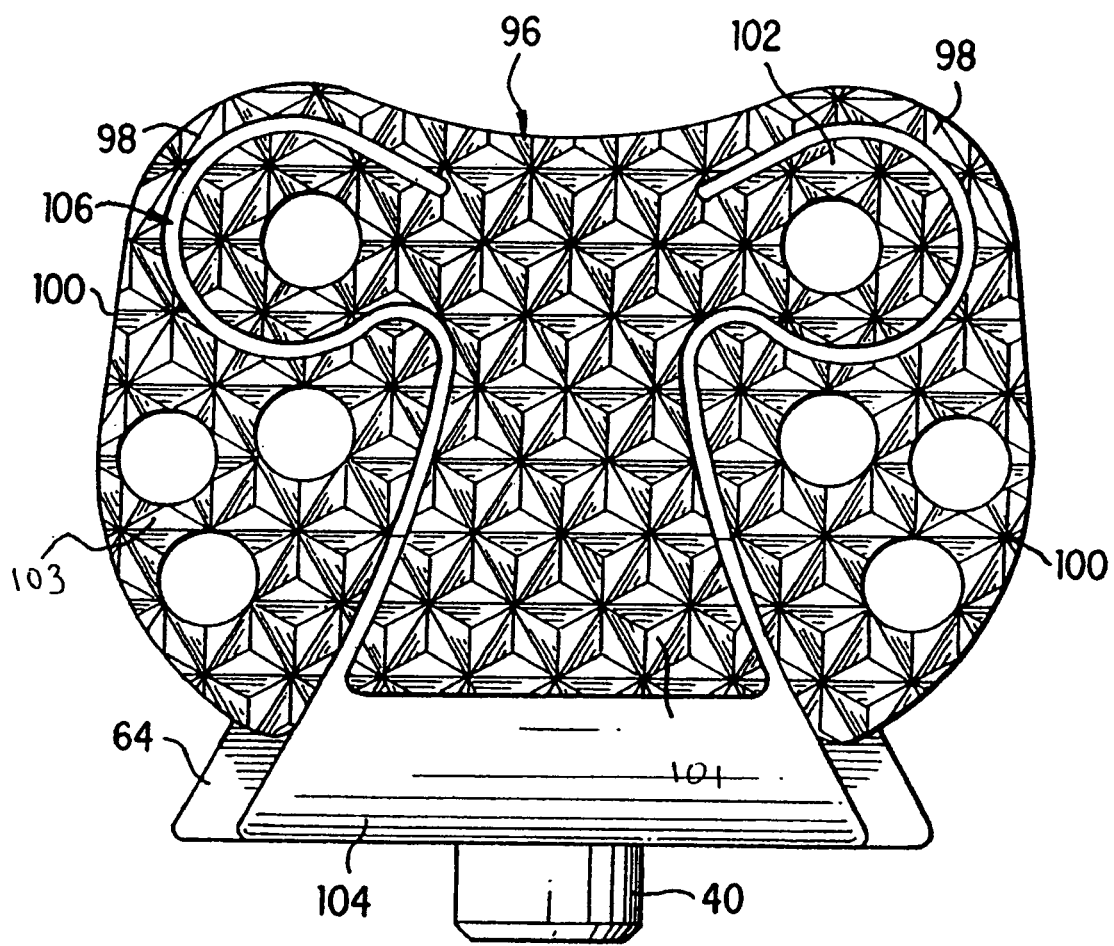
FIG. 9 is a top view of a further embodiment of the invention.

The embodiment of FIG. 9 has an uneven surface to improve gripping against the vertebral body 54 extending not only across the gripping portion 101, but also across the remainder of the axial end surface 103 of the endplate 96. The uneven surface can comprise a series of pointed shapes, such as pyramids or tetrahedrons. In this view, the lateral portions 100, including the living hinges 98 can be seen spaced from the central portion 102, and the gripping portion 101 by narrow gaps 106, which can be made by machining, and which can be completely collapsed. The gaps 106 extend generally along S-curves, curving in one direction around the lateral extensions of the central portion 102 and reversing the curve between the lateral portions 100 and the gripping portion 101. Several fusion holes 108 are provided in the lateral portions 100 and central portion 102, and may also be provided in the gripping portion 101, to foment growth therein of and fusion with the adjacent bone.

The living hinges 98 are narrower than the remainder of the lateral portions 100 to localize bending in the hinges 98. The lateral portions 100 extend laterally inwardly to contact the lateral walls of the wedge 104, thus having generally triangular platforms. The gripping portion 101 has lateral sides that are concave, to maximize the filling of the space between the lateral portions 100, preferably having a wider anterior side than posterior side.

Figure 10:
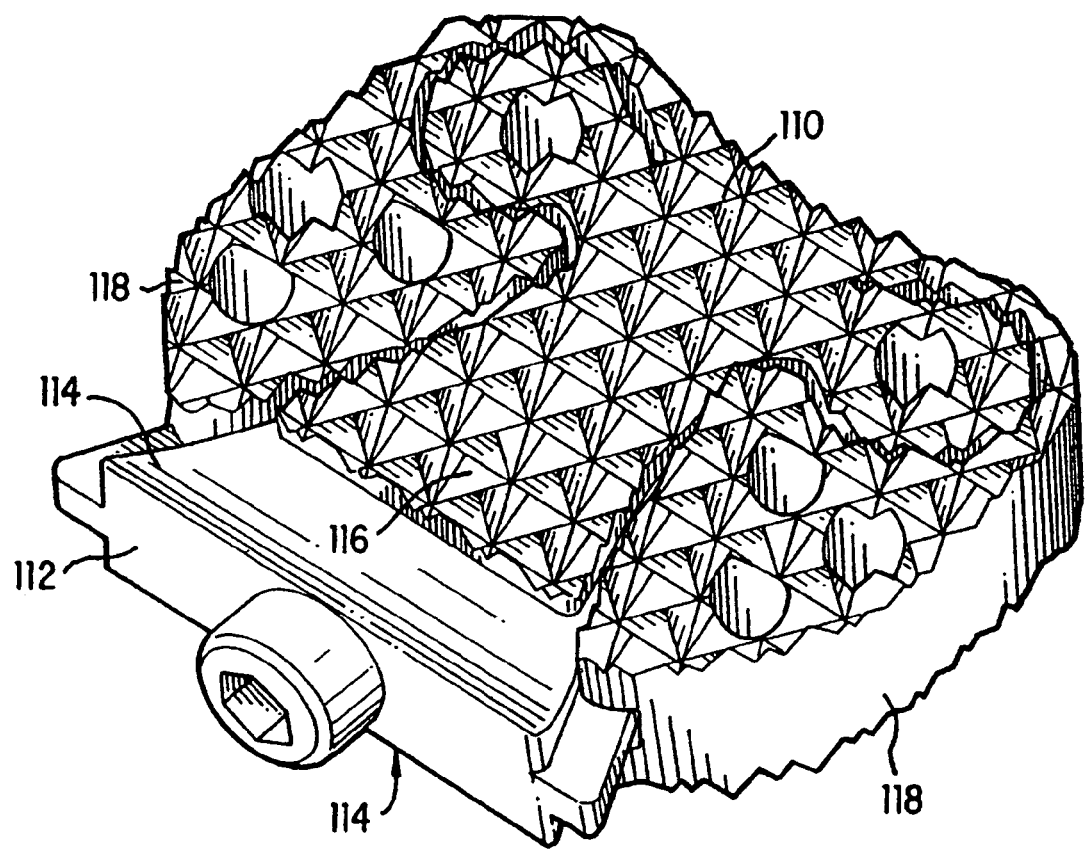
FIG. 10 is a top anterior perspective view of an embodiment of a cage constructed according to the invention.

Referring to FIG. 10, an embodiment of the invention is a fusion cage for fusion of adjacent vertebrae. This embodiment has a single endplate 110 that receives a wedge 112 that is tapered on top and bottom axial sides to extend top and bottom gripping portions 116. The endplate 110 has opposing axial end surfaces configured for supporting and abutting adjacent vertebrae when implanted. The lateral portions 118 are expanded when the cage is positioned between the vertebrae to contact the outer edge of the vertebral bodies.

Figure 12:
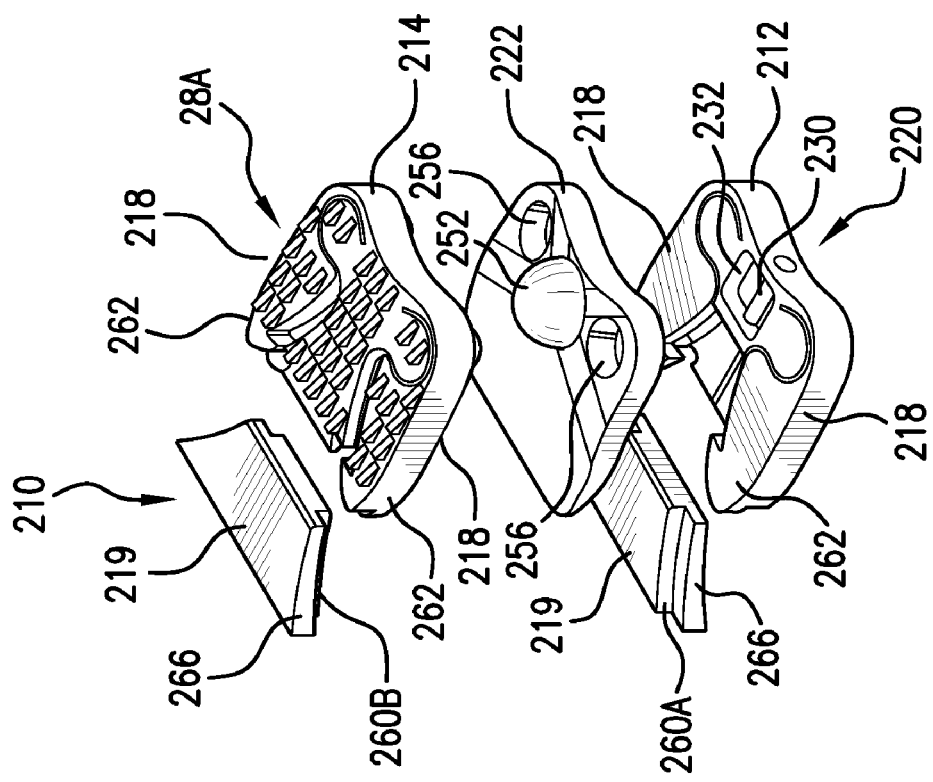
FIG. 12 is a bottom exploded view of the alternate embodiment of FIG. 11.
Figure 11:
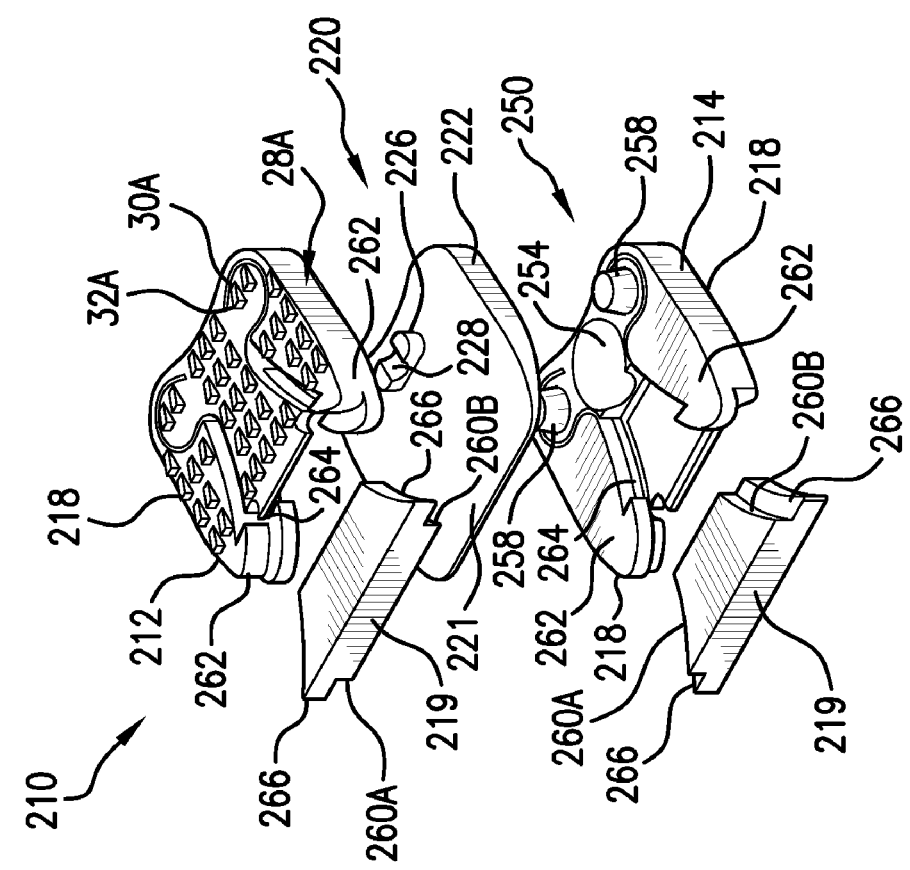
FIG. 11 is a top exploded view of an alternate embodiment.

Another embodiment of the vertebral disk prosthesis 210 is shown in FIGS. 11 and 12. This embodiment has additional or different features from those described above. It should be noted that the features of the alternate embodiments may be combined with, or substituted for, similar components on the other embodiments. For example, the embodiment of the vertebral disk prosthesis 210 is shown in FIG. 11. The top and bottom endplates 212, 214 include an additional, lateral plurality of scales 28A disposed on the lateral portions 218. The additional plurality of scales 28A may also be used on the first embodiment of the vertebral disk prosthesis 10 described above.

Turning to the embodiment in FIGS. 11 and 12, the vertebral disk prosthesis 210 includes members in the form of top and bottom endplates 212, 214, each having hinged lateral portions 218 and a wedge 219 and a spacer 220. The operation of the lateral portions 218, that is the movement between a contracted and an expanded position, is substantially similar to the operation of the lateral portions 18 described in the first embodiment above. The added features include the additional, lateral plurality of scales 28A, the addition of a pivot means 220, a relocation of the universal pivot components 250, and the use of a non-ratcheted wedge 219.

Addressing these components separately, the additional, lateral plurality of scales 28A, as with the scales 28, have a shallow ramp 30A on a posterior side thereof, to permit the introduction of the prosthesis 210 into the intervertebral space, and a steeper surface 32A, such as a vertical side to impede or prevent withdrawal of the prosthesis 210 from engagement with the vertebral body. The scales 28A, and preferably the lateral sides of the scales 28A, are preferably configured to resist lateral movement of the prosthesis 210 with respect to the adjacent vertebral body once implanted. Additionally, although shown in FIG. 11 as having a lateral thickness, the scales 28, 28A may also be very thin, or bladelike, along their longitudinal axis, thereby permitting the scales 28, 28A to more easily engage the vertebral body. It is further noted that in order to secure the vertebral disk prosthesis 210 to the vertebral bodies, the vertebral bodies may need to be immobilized or restrained from moving during the installation procedure. Such immobilization is performed as is known in the art.

The embodiment of the vertebral disk prosthesis 210 shown in FIGS. 11 and 12 also includes a lateral pivot means 220 between the top endplate 212 and the spacer 222. The spacer 222 is substantially similar to the spacer 66 described above. That is, the spacer 222 is made from the same materials, is substantially the same size, and serves substantially the same function as the spacer 66. The spacer 222 has a generally flat top side 221 and a tapered bottom side 223. The lateral pivot means 220 is disposed between the spacer upper side 221 and the top endplate 212. The pivot means 220 allows the top endplate 212 to pivot laterally relative to the spacer 222. As shown in FIG. 11, the pivot means 220, preferably, includes a pivot cradle 226 on the spacer top side 221. The pivot cradle 226 has a semi-cylindrical recess 228 extending generally in a direction between the anterior and posterior sides of the vertebral disk prosthesis 210. As shown in FIG. 12, the pivot means 220 also includes a pivot rod 230 disposed on the top endplate 212. The pivot rod 230 may be disposed in a recess 232. The recess 232 is sized to accommodate the pivot cradle 226. When the spacer 222 is disposed adjacent to the top endplate 212, the pivot cradle 226 is disposed within the recess 232 and the pivot rod 230 is disposed in the semi-cylindrical recess 228. In this configuration, the top endplate 212 may pivot laterally relative to the spacer 222. The extent of this rotation is generally minimal.

As also shown in FIGS. 11 and 12, in this embodiment of the vertebral disk prosthesis 210 the universal pivot components 250 have been relocated as compared to the first embodiment of the vertebral disk prosthesis 10 described above. That is, the spherical segment 252 is disposed on the spacer 222 bottom side 223 and the bottom endplate 214 includes a spherical socket 254. As with the first embodiment, the surface of the spacer 222 facing endplate 214 is, preferably, tapered. The spacer 222 also includes one or more lug recesses 256 (FIG. 12) on the bottom side 223. The lug recesses 256 are structured to engage two lugs 258 (FIG. 11) extending from the bottom end plate 214 towards the spacer 222. As before, the lugs 258 are configured to permit limited axial rotation between the endplates 212, 214. Preferably the lugs 258 extend generally axially from the endplate 214 and are tapered towards their tips. The socket 254 on the bottom endplate 214 preferably extends passed the major diameter of the spherical segment 252 to retain the spherical segment 252 in a snap-fit connection to prevent separation thereof and dislocation when implanted.

The embodiment of the vertebral disk prosthesis 210 also utilizes a non-ratcheted wedge 219. That is, neither the wedge 219 nor the lateral portions 218 include ratchet portions 52. Instead, the wedge 219 includes two, generally smooth, arcuate lateral sides 260A, 260B and the lateral portions 218 each form opposing locking pawls 262. There is one locking pawl 262 at the distal end of each lateral portion 218. The locking pawls 262 are structured to engage the anterior side of the wedge 219. In this embodiment of the vertebral disk prosthesis 210, the lateral width of vertebral disk prosthesis 210 is not adjustable. As such, there is also no need for a fastener 40 to adjust the wedge 219. Instead, the vertebral disk prosthesis 210 is inserted in the contracted position and the wedge 219 is introduced. As the wedge 219 is inserted, the lateral portions 218 flex outwardly, laterally until the anterior side of the wedge 219 passes the two opposing locking pawls 262. When the anterior side of the wedge 219 passes the two opposing locking pawls 262, the lateral portions 218 contract slightly and the locking pawls 262 engage the anterior side of the wedge 219. The wedge 219 may be supported axially by a portion of the prosthesis 210. Preferably, the lateral portions 218 include ledges 264 configured to slideably receive elongated keys 266 that protrude from the lateral sides of the wedge 219. The ledges 264 and keys 266 provide axial support to the wedge 219.

Figure 14:
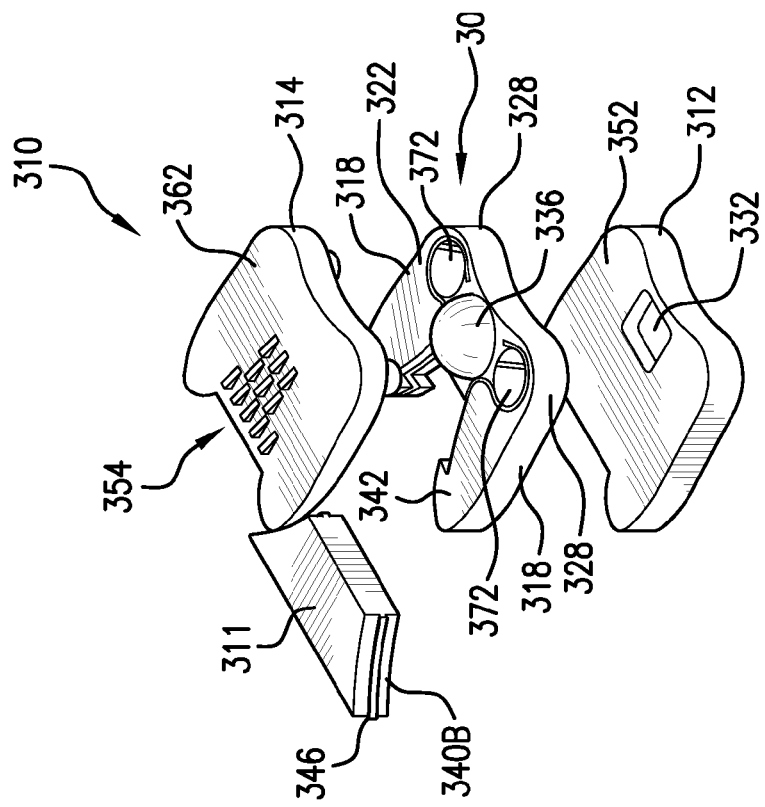
FIG. 14 is a bottom exploded view of the alternate embodiment of FIG. 13.
Figure 13:
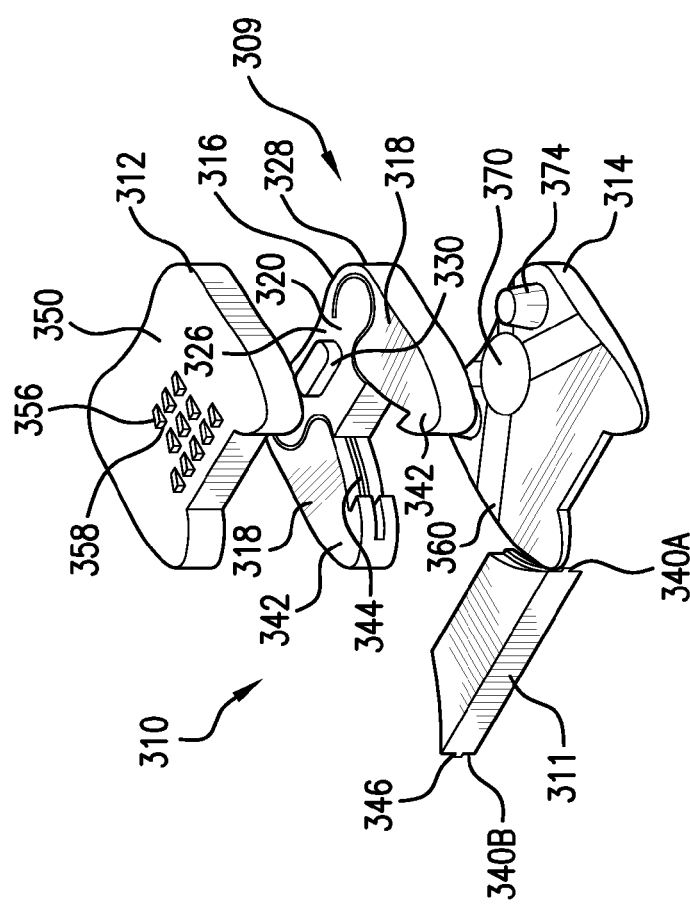
FIG. 13 is a top exploded view of an alternate embodiment.

Another embodiment of the vertebral disk prosthesis 310 is shown in FIGS. 13 and 14. In this embodiment, a member such as the spacer assembly 309, as opposed to the end plates 312, 314, includes the movable lateral portions 318. That is, the spacer assembly 309 includes a spacer body 316, having top and bottom axial sides 320 (FIG. 13), 322 (FIG. 14) as well as movable lateral portions 318, and a wedge 311. The wedge 311 is structured to engage and move the lateral portions 318. The spacer 310 body 316 has a center portion 326. Each lateral portion 318 is coupled to the center portion 326, preferably, by a living hinge 328. The living hinge 328 allows the lateral portions 318 to move between a first, contracted position to a second, expanded position. Although the spacer assembly 309 does not contact any vertebral body, it is still preferable for the spacer assembly 309 to expand to a size wherein the perimeter of the spacer assembly 309 is generally the same as the perimeter of an adjacent vertebral body. As before, the spacer assembly 309 is, preferably, made from a resilient material as described above.

The spacer body top and bottom axial sides 320, 322 are generally parallel. The spacer body top axial side 320 includes a tab 330 on the center portion 326. The tab 330 is, preferably, generally rectangular and extends between above the spacer body top axial side 320. The tab 330 is structured to engage a tab recess 332 (FIG. 14) on the top end plate 312. The spacer body bottom axial side 322 includes a spherical segment 336 structured to engage a spherical socket 370 on the bottom endplate 314.

The spacer assembly 309 also utilizes a non-ratcheted wedge 311. That is, neither the wedge 311 nor the spacer body lateral portions 318 include ratchet portions 52. Instead, the wedge 311 includes two, generally smooth, arcuate lateral sides 340A, 340B and the lateral portions 318 each form opposing locking pawls 342. There is one locking pawl 342 at the distal end of each lateral portion 318. The locking pawls 342 are structured to engage the anterior side of the wedge 311. In this embodiment of the vertebral disk prosthesis 310, the lateral width of vertebral disk prosthesis 310 is not adjustable. As such, there is also no need for a fastener 40 to adjust the wedge 311. Instead, the vertebral disk prosthesis 310 is inserted in the contracted position and the wedge 311 is introduced. As the wedge 311 is inserted, the spacer body lateral portions 318 flex outwardly, laterally until the anterior side of the wedge 311 passes the two opposing locking pawls 342. When the anterior side of the wedge 311 passes the two opposing locking pawls 342, the lateral portions 318 contract slightly and the locking pawls 342 engage the anterior side of the wedge 311. The wedge 311 may be supported axially by a portion of the spacer body 316. Preferably, the lateral portions 318 include keyways 344 configured to slideably receive elongated keys 346 that protrude from the wedge lateral sides 340A, 340B. The keyways 344 and keys 346 provide axial support to the wedge 311. As before, the location of the keyways 344 and the keys 346 on the spacer body 316 and the wedge 311 may be reversed. Also, as before, the wedge 311 is tapered in the axial direction so that, as the wedge is inserted between the lateral portions 318, the wedge 311 engages the endplates 312, 314 which are moved axially. The vertebral bodies may need to be immobilized or restrained from moving during the installation procedure. Such immobilization is performed as is known in the art.

The top end plate 312 has a top side 350 (FIG. 13) and a bottom side 352 (FIG. 14). The bottom end plate 314 has a top side 360 (FIG. 13) and a bottom side 362 (FIG. 14). The top endplate top side 350 and the bottom endplate bottom side 362 each include a plurality of scales 354. As with the scales 28 described above, the top endplate top side scales 354 have a shallow ramp 356 on a posterior side thereof, to permit the introduction of the prosthesis 310 into the intervertebral space, and a steeper surface 358, such as a vertical side to impede or prevent withdrawal of the prosthesis 310 from engagement with the vertebral body. The scales 354 are preferably configured to resist lateral movement of the prosthesis 310 with respect to the adjacent vertebral body once implanted. The scales 354 are disposed on the medial, anterior portion of the top endplate top side 350 and the bottom endplate bottom side 362, generally adjacent to the portion of the endplates 312, 314 engaged by the wedge 311. Additionally, although shown in FIGS. 13 and 14 as having a lateral thickness, the scales 354 may also be very thin, or bladelike, along their longitudinal axis, thereby permitting the scales 354 to more easily engage the vertebral body.

As shown on FIG. 14, the top endplate bottom side 352 includes a tab recess 332 structured to engage the tab 330 on the spacer body top axial side 320. The tab recess 332, preferably, has a greater width in the anterior-posterior direction than the tab 330. The tab recess 332 is wider than the tab 330. Thus, the spacer assembly 309 may move slightly in the anterior-posterior direction relative to the top endplate 312.

As shown on FIG. 13, the bottom endplate top side 360 includes a spherical socket 370 and, preferably, two lugs 374. Additionally, in this embodiment, the bottom endplate top side 360 is, preferably, tapered in a manner similar to the taper of the spacer 66 described above with respect to embodiment shown in FIG. 1. As shown in FIG. 14, the spacer body bottom side 322 includes two lug recesses 372 that are structured to engage the two lugs 374 extending from the bottom end plate top side 360 towards the spacer body bottom side 322. As before, the lugs 374 are configured to permit limited axial rotation between the endplates 312, 314. Preferably the lugs 374 are tapered towards their tips. The spherical socket 370 on the bottom endplate 314 preferably extends passed the major diameter of the spherical segment 336 to retain the spherical segment 336 in a snap-fit connection to prevent separation thereof and dislocation when implanted.

Figure 16:
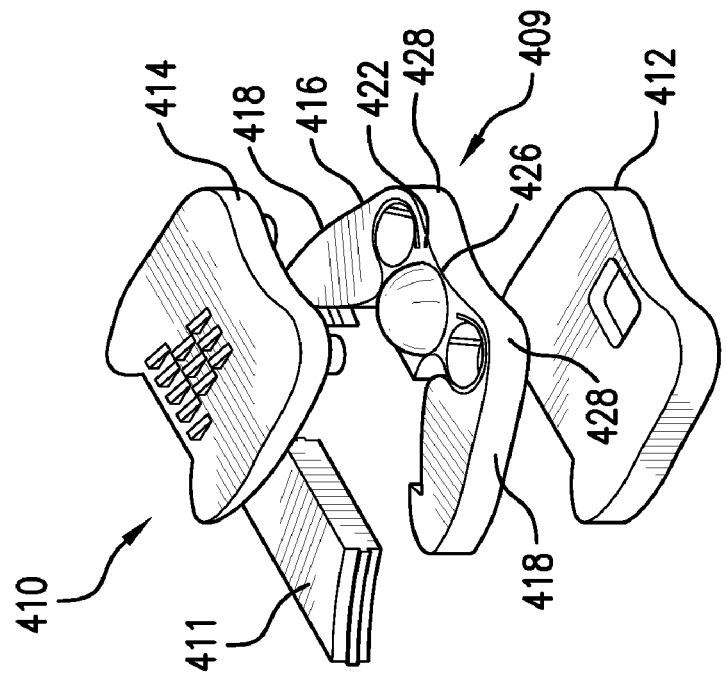
FIG. 16 is a bottom exploded view of the alternate embodiment of FIG. 15.
Figure 15:
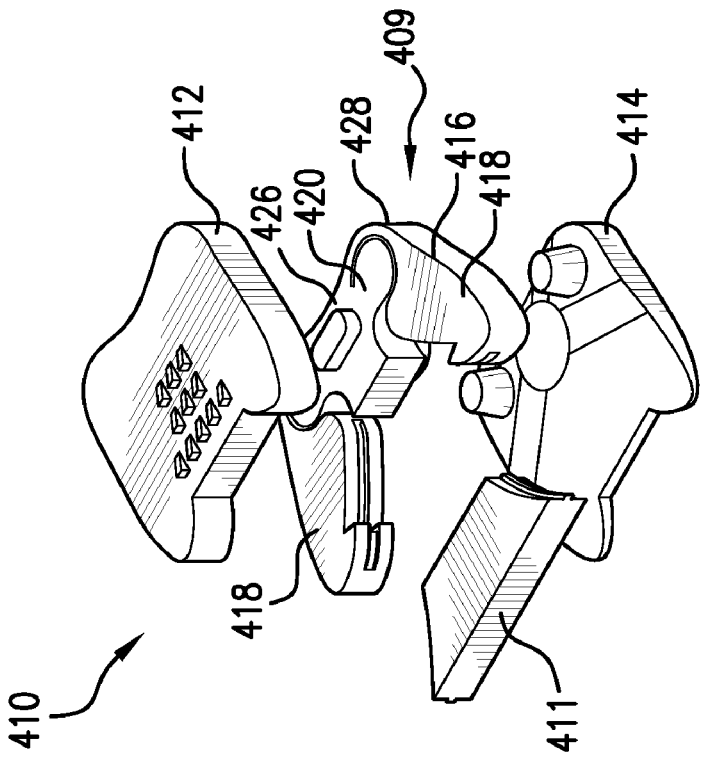
FIG. 15 is a top exploded view of an alternate embodiment.

Another embodiment of the vertebral disk prosthesis 410 is shown in FIGS. 15 and 16. The embodiment shown in FIGS. 15 and 16 is substantially similar to the embodiment shown in FIGS. 13 and 14 and like reference numbers will be used to denote like elements but are increased by "100." Thus, there is a spacer assembly 409, as opposed to the endplates 412,414, includes the movable lateral portions 418. That is, the spacer assembly 409 includes a spacer body 416, having top and bottom axial sides 420 (FIG. 15), 422 (FIG. 16) as well as movable lateral portions 418, and a wedge 411. The wedge 411 is structured to engage and move the lateral portions 418. The spacer assembly body 416 has a center portion 426. Each lateral portion 418 is coupled to the center portion 426, preferably, by a living hinge 428. Unlike the living hinge 328 of the embodiment shown in FIG. 13, however, the living hinge 428 of this embodiment is biased in a semi-expanded position. That is, while the living hinge 428 still allows the lateral portions 418 to move between a first, contracted position to a second, expanded position, the natural bias of the living hinge 428 is toward the second, expanded position, but not fully expanded.

To insert this embodiment of the vertebral disk prosthesis 410 in a patient, the surgeon must manually squeeze the lateral portions 418 to the first, contracted position as the vertebral disk prosthesis 410 is passed through the perimeter of the annulus fibrosus. Once in place between two vertebral bodies, the spacer body lateral portions 418 are biased to a semi-expanded position. In this position, insertion of the wedge 411 is easier to accomplish. The remaining features of this embodiment of the vertebral disk prosthesis 410 are substantially similar to the embodiment of the vertebral disk prosthesis 310 shown in FIGS. 13 and 14.

The expansion member does not have to be a wedge and the lateral portions do not have to be coupled by living hinges. As shown in FIGS. 17–19, an alternate embodiment of the vertebral disk prosthesis 510 includes a member 511 with pivotally hinged lateral portions 518. The following description addresses a bottom endplate 514, as shown in FIG. 17, but it is understood that a top endplate 512 (FIG. 18) is constructed in a similar manner. The bottom endplate 514 includes a center portion 516 and two pivotally, hinged lateral portions 518. The center portion 516 houses a worm drive assembly 520. The worm drive assembly 520 includes an actuating rod 522 and two expansion rods 524 (one shown). The actuating rod 522 threadably engages the two expansion rods 524 and is structured so that rotation of the actuating rod 522 causes the expansion rods 524 to move laterally into or out of the center portion 516. The lateral portions 518 include a landing 528 that is a flat surface disposed adjacent to an expansion rod 524 when the lateral portion 518 is coupled to the center portion 516.

The lateral portions 518 are coupled to the center portion 516 by pivot pins 530. That is, both the lateral portions 518 and the central portion 516 include pivot pin openings 532, 534 (respectively). The pivot pins 530 pass through both the center portion openings 534 and the lateral portion openings 532, thereby pivotally coupling the lateral portions 518 to the center portion 516. In this configuration, the lateral portion landings 528 are each disposed adjacent to an expansion rod 524. Thus, when the worm drive assembly 520 is actuated to move the expansion rods 524 out of the center portion 516, the expansion rod 524 contacts the lateral portions 518 and moves the lateral portions 518 from a first, contracted position to a second, expanded position.

The center portion 516 may also include a pivot limiting device 540. The pivot limiting device 540 may be formed by the perimeter shape of the center portion 516 and the lateral portions 518. That is, both the center portion 516 and the lateral portions 518 may include projections 542, 544 (respectively). The projections 542, 544 are shaped so that, when the lateral portions 518 are coupled to the center portion 516, as the lateral portions 518 move to a desired lateral width, the projections 542, 544 contact each other thereby limiting further lateral expansion.

As shown in FIGS. 18 and 19, the embodiment of the shown in FIG. 17 vertebral disk prosthesis member 511 may be used in a vertebral disk prosthesis 510 that incorporates any of the components, e.g. a universal pivot, described above. That is, as shown, the vertebral disk prosthesis 510 may include a spacer 570 that is substantially similar to the spacer 222 described in relation to the embodiment shown in FIGS. 11 and 12. The endplates 512, 514 are coupled to the spacer 570 in a manner substantially similar to the spacer 222 described in relation to the embodiment shown in FIGS. 11 and 12.

While illustrative embodiments of the invention are disclosed herein, it will be appreciated that numerous modifications and other embodiments may be devised by those skilled in the art. For example, the lateral portions do not have to rotate or flex at, or near, the posterior side of the member. For example, the lateral portions may be structured to translate laterally from a contracted position to an expanded position. Therefore, it will be understood that the appended claims are intended to cover all such modifications and embodiments that come within the spirit and scope of the present invention.

What is claimed is:

1. A vertebral disk prosthesis structured to be disposed adjacent to at least one vertebral body, said vertebral body having a periphery, said vertebral disk prosthesis comprising:
at least one contacting member including a top endplate and a bottom endplate and having at least two movable lateral portions, said lateral portions coupled to each other; the top endplate structured to engage a first vertebral body and the bottom endplate structured to engage a second vertebral body, wherein the top and bottom endplates are pivotally connected for allowing the adjacent vertebral bodies to pivot with respect to each other when the endplates are engaged with the vertebral bodies;
said lateral portions movable between:
a contracted position in which the lateral portions are disposed such that the member has a first lateral width, said first lateral width being smaller than the lateral width of a vertebral body of a patient; and
an expanded position in which the lateral portions are disposed such that the contacting member has a second lateral width that is larger than the first lateral width, and said at least one axial end surface is configured for supporting and abutting the periphery of the vertebral body, the second lateral width being sufficient for the axial end surface on the lateral portions to support and abut said periphery at opposite lateral sides of the vertebral body;
an expansion member disposed between said lateral portions and configured for moving said lateral portions between the contracted position and the expanded position; and
a bushing that comprises a gel disposed and in supportive association between said top and bottom endplates.

2. The prosthesis of claim 1, wherein the shape of the member in the expanded position generally corresponds to the periphery of the vertebral body.

3. The prosthesis of claim 2, wherein in the expanded position the lateral portions are configured for abutting and supporting at least about 75% of the periphery of the vertebral body.

4. The prosthesis of claim 1, wherein said lateral portions are flexibly coupled to each other for moving between the contracted and the expanded position.

5. The prosthesis of claim 4, wherein said lateral portions are normally biased to the contracted position and must be acted upon by said expansion member to be moved to said expanded position.

6. The prosthesis of claim 4, wherein said lateral portions are normally biased to a semi-expanded position and must be acted upon by said expansion member to be moved to said expanded position.

7. The prosthesis of claim 1, wherein:
said at least one member further includes a central portion; and
said lateral portions are movably coupled to said central portion.

8. The prosthesis of claim 1, wherein in the expanded position said lateral portions are configured for abutting and supporting at least about 50% of the periphery of the vertebral body.

9. The prosthesis of claim 1, wherein said at least one member comprises a cage configured for locking adjacent vertebral bodies together, and said axial end surface comprises first and second axial end surfaces facing in opposite directions for abutting and supporting the adjacent vertebral bodies.

10. The prosthesis of claim 1, wherein each of said top and bottom endplates comprises a central portion disposed between said lateral portions, wherein the central portions are pivotally connected to each other.

11. The prosthesis of claim 1, wherein the lateral portions are movably coupled by a living hinge.

12. The prosthesis of claim 11, wherein:
said living hinge comprises first and second living hinges connected to the lateral portions, respectively; and
said at least one member comprises a central portion coupled to each said living hinges.

13. A vertebral disk prosthesis, comprising:
a top endplate configured to supportively engage a first vertebral body; and
a bottom endplate configured to supportively engage a second vertebral body, wherein the top and bottom endplates are pivotally connected for allowing the adjacent vertebral bodies to pivot with respect to each other when the endplates are engaged therewith;
wherein each endplate comprises:
lateral portions connected to each other for movement in vertebral lateral directions between:
a contracted position in the implantation configuration, in which the body of said at least one member has a first lateral width and the end surface is narrower than the lateral width of a vertebral body of a patient,
an expanded position in the implanted configuration, in which the lateral portions are disposed such that said at least one member has a second lateral width that is larger than the first lateral width, and in which the axial end surface is configured for supporting and abutting the body; and
an axial portion configured for moving with respect to the lateral portions in a vertebral axial direction away from the other of the endplates from:
a retracted position in the implantation configuration, in which the prosthesis has a first axial height, and
to an extended position in the implanted configuration, in which the prosthesis has a second axial height that is greater than the first axial height.

14. The prosthesis of claim 13, wherein:
the lateral portion of each endplate comprise a first wedge support portion and the wedge comprises a second wedge support portion;
the prosthesis further comprises top and bottom wedges, each of which is receivable between said lateral portions of the top and bottom endplates, respectively, for moving said lateral portions and axial portion of the respective top and bottom endplate between the contracted and expanded positions and the retracted and extended position; and
the top and bottom wedges are supported in the vertebral axial direction by the wedge support portions of the lateral portions of the top and bottom endplates, respectively, to bias each axial portion in towards the extended position.

15. The prosthesis of claim 14, further comprising:
a top threaded fastener connected between the top wedge and top endplate; and
a bottom threaded fastener connected between the bottom wedge and bottom endplate;
wherein rotation of the top and bottom threaded fasteners respectively moves said top and bottom wedges with respect to said top and bottom endplates whereby said lateral portions of the respective edgeplates are moved between the contracted position and the expanded position.

16. A prosthetic device, comprising:
the prosthesis of claim 7; and
an instrument for implanting the prosthesis, which instrument comprises:
top and bottom fastener drivers respectively configured for engaging and driving the top and bottom fasteners for adjusting the width of the first and second endplates; and
a spacer connected between the first and second drivers and configured and dimensioned for positioning between first and second endplates, wherein the spacer is configured for maintaining the relative position of the endplates.

17. The instrument of claim 16, wherein the drivers are substantially parallel.

18. The instrument of claim 16, wherein the drivers are adapted to substantially simultaneously engage both fasteners.

19. The instrument of claim 16, further comprising a releasable locking mechanism adapted to releasably secure the implantation instrument to the prosthesis.

20. The instrument of claim 19, wherein the fasteners each define an internal groove, and wherein a releasable locking mechanism further comprises a locking ball adapted to be received by the groove, and a sliding cam for controlling the position of the locking balls.

21. The prosthesis of claim 14, wherein said lateral portions are normally biased to the contracted position and must be acted upon by said wedges to be moved to said expanded position.

22. The prosthesis of claim 14, wherein said lateral portions are normally biased to a semi-expanded position and must be acted upon by said wedges to be moved to said expanded position.

23. The prosthesis of claim 13, wherein the axial portion of each of the top and bottom endplates is a single axial portion.

24. The prosthesis of claim 13, wherein the top and bottom endplates are pivotally connected for allowing the adjacent vertebral bodies to pivot in vertebral flexion, extension, lateral bending, and axial rotation with respect to each other when the endplates are engaged therewith.

25. The prosthesis of claim 13, wherein at least one of the endplates comprises a wedge receivable between said lateral portions for moving said lateral portions between the contracted position and the expanded position.

26. The prosthesis of claim 25, wherein said wedge has a laterally elongated cross-section extending along a plane normal to a direction of movement of said wedge.

27. The prosthesis of claim 25, wherein said wedge includes an axial surface that is inclined with respect to the plane of the axial surface for moving the axial portion of the at least one endplate to the extended position.

28. The prosthesis of claim 25, wherein said wedge and at least one of the endplates are associated for resisting withdrawal movement of said wedge with respect to said at least one of the endplates to resist said lateral portions from moving towards the contracted position.

29. The prosthesis of claim 25, wherein said wedge and said at least one of the endplates comprise a ratchet configured for allowing movement of said wedge with respect to said lateral portions in a first direction for moving said lateral portions to the expanded position and for restricting or resisting movement of said wedge in an opposite direction.

30. The prosthesis of claim 25, wherein the lateral portions comprise a first wedge support portion and the wedge comprises a second wedge support portion, one of the wedge support portions comprising a key and the other comprising a keyway configured and dimensioned for slideably receiving the key to provide axial support to the wedge.

31. The prosthesis of claim 13, further comprising a pivot limiter disposed between said top and bottom endplates and comprising a sloped surface facing one endplate, wherein said top endplate and said the pivot limiter are pivotally connected and the sloped surface is configured and associated with said top and bottom endplates for allowing and limiting pivoting between the top endplate and the pivot limiter.

32. The prosthesis of claim 13, further comprising:
a pivot that pivotally connects said top and bottom endplates for vertebral axial rotation substantially about a vertebral longitudinal axis; and
at least one protrusion associated with one of said top and bottom endplates and received in an opening of the other of the said top and bottom endplates, wherein the opening is larger than the protrusion for permitting and limiting the axial rotation.

33. The prosthesis of claim 32, wherein the pivot comprises a universal pivot.

34. The prosthesis of claim 13, further comprising a spacer disposed between said top and bottom endplates.

35. The prosthesis of claim 34, wherein:
said spacer includes a central portion; and
said lateral portions movably coupled to said central portion.

36. The prosthesis of claim 13, wherein the axial portion comprises a gripping portion disposed and configured for engaging and gripping an interior portion of the vertebral body face in the expanded position.

37. The prosthesis of claim 13, further comprising an expansion member associated with lateral and axial portions for moving the lateral and axial portions to the expanded and extended positions.

38. The prosthesis of claim 37, wherein the expansion member comprises a wedge with lateral and axial wedge surfaces cammingly associated with the lateral and axial portions for camming to the expanded and extended positions.

39. The prosthesis of claim 13, further comprising a bushing disposed between and in supportive association with the endplates when the prosthesis is implanted between the vertebral bodies, wherein the bushing comprises a gel and is configured for absorbing shock between the adjacent vertebral bodies.

40. The prosthesis of claim 39, wherein the bushing is slideable with respect to at least one of the endplates for reducing shearing within the bushing during relative motion between the first and second endplates.

* * * * *